(12) United States Patent
Kaneko et al.

(10) Patent No.: US 8,216,247 B2
(45) Date of Patent: Jul. 10, 2012

(54) ENDOSCOPIC INSTRUMENT AND METHOD FOR MANUFACTURING

(75) Inventors: Tatsuya Kaneko, Tokyo (JP); Megumi Kimura, Tokyo (JP); Kazunari Kagawa, Tokyo (JP); Kenji Fujiwara, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 11/924,271

(22) Filed: Oct. 25, 2007

(65) Prior Publication Data

US 2009/0112225 A1    Apr. 30, 2009

(51) Int. Cl.
*A61B 17/26* (2006.01)
(52) U.S. Cl. ........................................ 606/113
(58) Field of Classification Search .............. 600/101, 600/104, 106, 137; 606/110, 113–114, 127–128, 606/167, 170, 180, 47
See application file for complete search history.

(56) References Cited

U.S. PATENT DOCUMENTS

| | | | |
|---|---|---|---|
| 3,955,578 A * | 5/1976 | Chamness et al. | 606/47 |
| 5,064,428 A * | 11/1991 | Cope et al. | 606/127 |
| 6,933,847 B2 | 8/2005 | Feibelman | |
| 2002/0010485 A1 | 1/2002 | Griego et al. | |

FOREIGN PATENT DOCUMENTS

| | | |
|---|---|---|
| EP | 1 815 810 A1 | 8/2007 |
| EP | 1 849 419 A1 | 10/2007 |
| JP | 9-201367 | 8/1997 |
| JP | 11-070122 | 3/1999 |
| WO | WO 00/42926 | 7/2000 |
| WO | WO 2006/088148 A1 | 8/2006 |

OTHER PUBLICATIONS

U.S. Office Action dated Sep. 26, 2011 received in related U.S. Appl. No. 12/856,256.

* cited by examiner

*Primary Examiner* — Ryan Severson
*Assistant Examiner* — Ashley Cronin
(74) *Attorney, Agent, or Firm* — Scully, Scott, Murphy & Presser, P.C.

(57) ABSTRACT

An endoscopic instrument according to the present invention includes: a wire disposed in a flexible sheath and capable of freely projecting relative to the flexible sheath, the distal end of the wire expanding in radius to form a loop section or a basket section upon being projected from the sheath; and a fixture cylinder for fixing the inserted proximal end of the wire, wherein the fixture cylinder is provided with a wire-radius-increasing-direction-regulating section for regulating the direction in which the radius of the wire increases; and a wire-fixing section, disposed in the vicinity of the proximal end relative to the wire-radius-increasing-direction-regulating section, for fixing the wire.

8 Claims, 9 Drawing Sheets

ENDOSCOPIC INSTRUMENT AND METHOD FOR MANUFACTURING

BACKGROUND OF THE INVENTION

1. Field of the Invention

The present invention relates to an endoscopic instrument and a method for manufacturing thereof.

2. Background Art

A snare for use in endoscopic polypectomy conducted in a body cavity is a wire bent in a U-shape to form a loop having a proximal end connected to a maneuvering wire capable of extending and retracting in a sheath. Maneuvering, e.g. retracting the maneuvering wire, causes the loop section to be retracted into a distal end of the sheath, thereby reducing the radius of the loop which is constricting a polyp or discharging a high-frequency electric current if necessary.

The proximal end of a snare wire of such kind is inserted into a metal fixture cylinder as disclosed by Japanese Unexamined Patent Application, First Publication No. H9-201367 and fixed to the fixture cylinder in one unit by filling a brazing filler metal or solder into the fixture cylinder or by crimping the fixture cylinder. To be more specific, a fixture specially designed for maintaining a position, e.g., a direction of the loop plane projecting from the sheath is used for fixing the proximal end of the snare wire to the fixture cylinder.

SUMMARY OF THE INVENTION

An object of the present invention is to provide an endoscopic instrument and a method for manufacturing the endoscopic instrument that can fix the proximal end of a wire to a fixture cylinder and regulate a wire-radius-increasing-direction upon projecting the distal end of a wire from the sheath.

An endoscopic instrument according to an aspect of the present invention includes: a wire disposed in a flexible sheath and capable of freely projecting relative to the flexible sheath, the distal end of the wire expanding in radius to form a loop section or a basket section upon being projected from the sheath; and a fixture cylinder for fixing the inserted proximal end of the wire, wherein the fixture cylinder is provided with a wire-radius-increasing-direction-regulating section for regulating the direction in which the radius of the wire increases; and a wire-fixing section, disposed in the vicinity of the proximal end relative to the wire-radius-increasing-direction-regulating section, for fixing the wire.

A method according to an aspect of the present invention for manufacturing an endoscopic instrument including a wire disposed in a flexible sheath and capable of freely projecting relative to the flexible sheath, the distal end of the wire expanding in radius to form a loop section or a basket section upon being projected from the sheath includes: a step for inserting a proximal end of the wire into a metal fixture cylinder; a first-crimping step for crimping the fixture cylinder to form a wire-radius-increasing-direction-regulating section which regulates the direction in which the radius of the wire increases upon forming a loop section or a basket section; and a second-crimping step for forming a wire-fixing section for fixing the wire by crimping the vicinity of the proximal end relative to the wire-radius-increasing-direction-regulating section of the fixture cylinder.

PREFERRED EMBODIMENTS

Embodiments will be hereafter explained in detail.

Structural elements that are equivalent in the following explanation will be assigned the same numeric symbols and redundant explanations thereof will be omitted.

Figure 1:
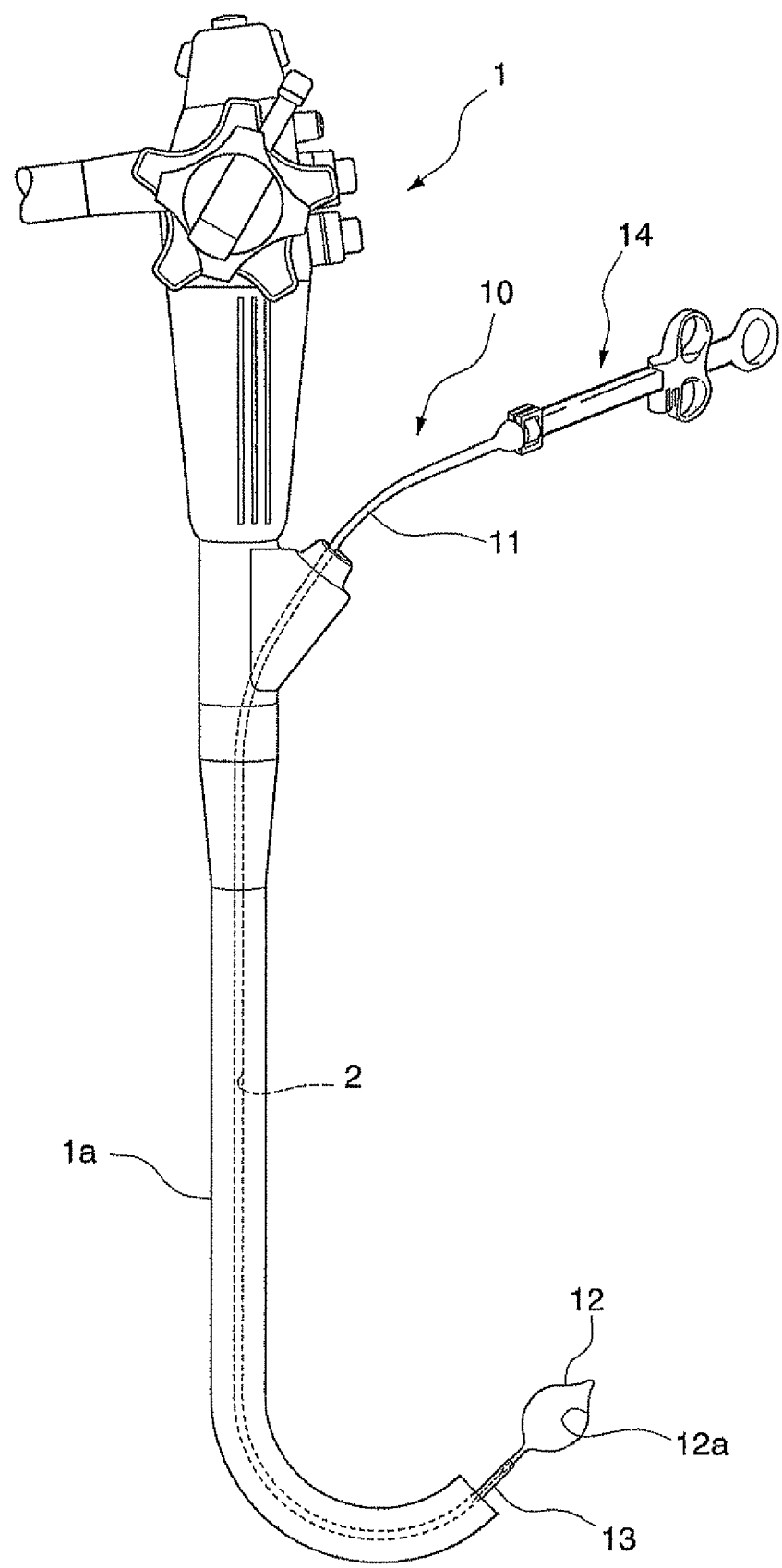
FIG. 1 is a perspective view of an endoscopic instrument inserted into a channel of an endoscope according to an embodiment of the present invention.

FIG. 1 is a perspective view of an endoscopic instrument inserted into a channel of an endoscope. In the drawing, reference numeral 1 indicates an endoscope. The endoscope 1 has an insertion section 1a having a channel 2 that allows part of an endoscopic instrument 10 to extend or retract therethrough.

The endoscopic instrument 10 includes a flexible sheath 11 inserted through the channel 2 of the endoscope; a high-frequency incision wire 12 capable of freely projecting or retracting relative to the sheath 11; and a maneuvering section 14 for increasing or reducing the radius of the high-frequency incision wire 12 via a maneuvering wire 13.

The sheath 11 is made of resin electrically insulative and harmless to humans, e.g., polytetrafluoroethylene. In addition, the outer radius of the sheath 11 is set to allow insertion thereof into the channel 2 of the endoscope 1; and the inner radius is set to allow insertion of the high-frequency incision wire 12 therethrough.

Figure 2:
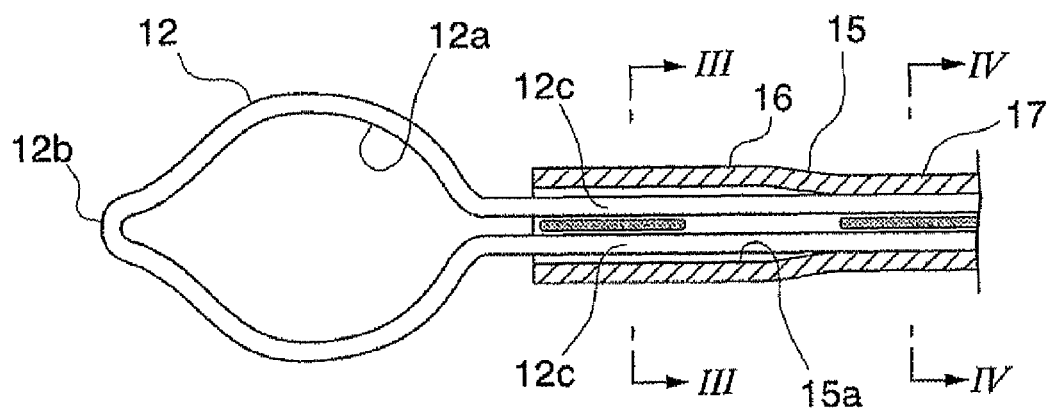
FIG. 2 is a cross-section showing the structure of a distal end of the endoscopic instrument.
Figure 3:
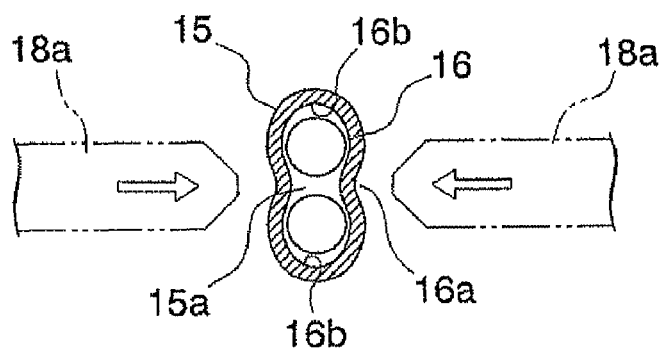
FIG. 3 is a cross-sectional view taken along a line III-III in FIG. 2.
Figure 4:
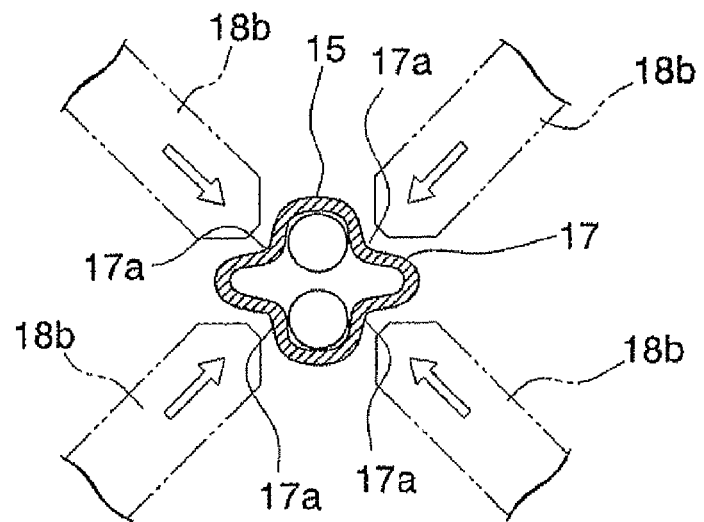
FIG. 4 is a cross-sectional view taken along a line IV-IV in FIG. 2.

FIG. 2 is a cross-sectional view showing the structure where the high-frequency incision wire is fixed to the fixture cylinder; FIG. 3 is a cross-sectional view taken along the line III-III in FIG. 2; and FIG. 4 is a cross-sectional view taken along the line IV-IV in FIG. 2.

As illustrated in the drawings, the distal end of the high-frequency incision wire 12 having a precurve pushed out of the sheath 11 expands to form a loop section 12a. In addition, a folding section 12b is formed on the center of the distal end of the high-frequency incision wire 12. Furthermore, the proximal end of the high-frequency incision wire 12 has two end sections 12c and 12c inserted and fixed in the fixture cylinder 15.

In the present specification, it should be noted that a "distal end" indicates an end having the high-frequency incision wire 12 attached to the endoscopic instrument 10; and a "proximal end" indicates an end having the maneuvering section 14 attached to the endoscope instrument 10.

Figure 5:
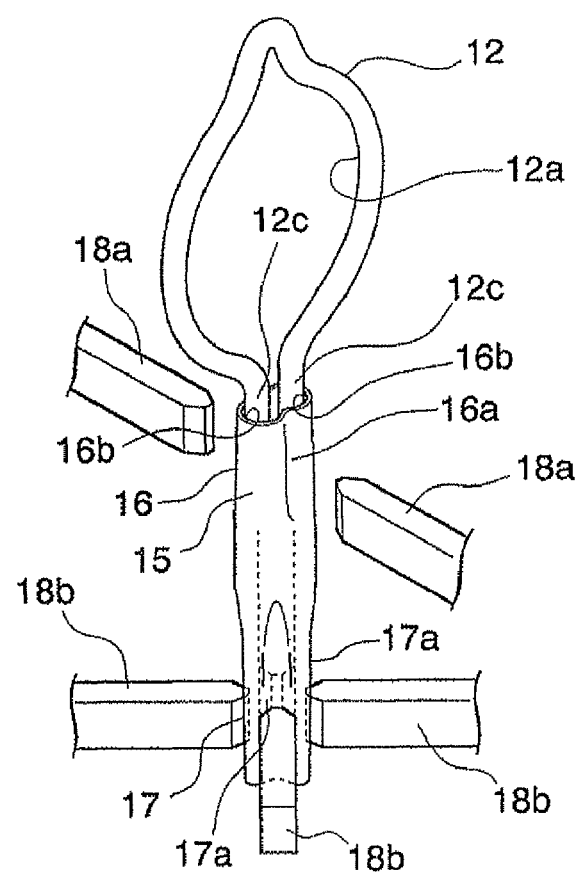
FIG. 5 is a perspective view showing how to manufacture the endoscopic instrument according to the embodiment.
Figure 6:
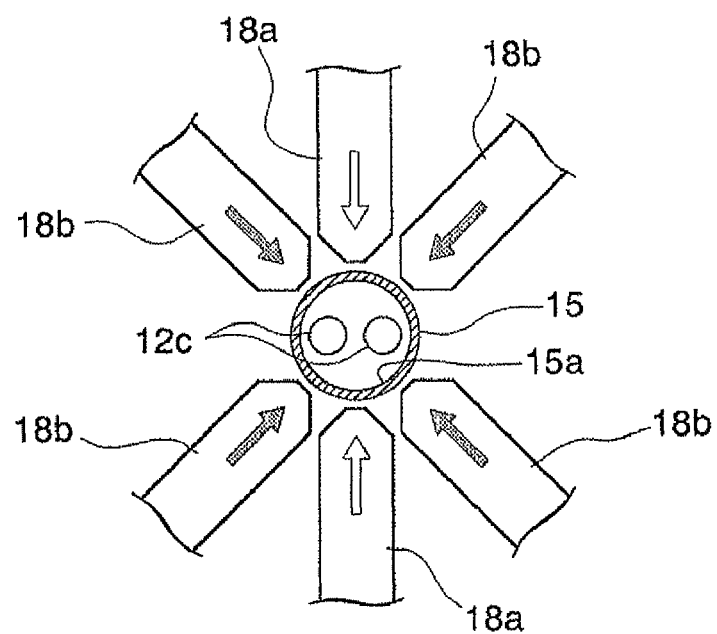
FIG. 6 is a cross sectional view showing how to manufacture the endoscopic instrument according to the embodiment.

The fixture cylinder 15 is provided with a wire-radius-increasing-direction-regulating section 16, disposed to the distal end, for regulating the direction in which the radius of the high-frequency incision wire 12 increases; and a wire-fixing section 17, disposed in substantially the middle of longitudinal direction, for fixing the two end sections 12c and 12c of the high-frequency incision wire 12. The fixture cylinder 15 is made from metal material, e.g., stainless steel. As illustrated in FIG. 5, extruding punches 18a and 18a in two opposed directions to crimp the two end sections 12c and 12c inserted through a hole 15a at the proximal end of the high-frequency incision wire 12 allows the wire-radius-increasing-direction-regulating section 16 to be formed. In addition, extruding punches 18b in four directions each shifted by 90 degrees and crimping the fixture cylinder 15 form a wire-fixing section 17. FIG. 5 is a perspective view showing how to crimp the fixture cylinder 15 by the punches 18a and 18b. The fixed state of two end sections 12c and 12c of the high-frequency incision wire 12 as illustrated in FIG. 5 reach the wire-fixing section 17 of the fixture cylinder 15.

The wire-radius-increasing-direction-regulating section 16 formed by the punches 18a crimping in two opposed directions has, in total, two recessing sections 16a shifted by 180 degrees on the outer periphery thereof. Also, the wire-fixing section 17 formed by the punches 18b crimping in four directions each shifted by 90 degrees has, in total, four recessing sections 17a on the outer periphery thereof. It should be noted that the punches 18b undertaking crimping of the wire-fixing section 17 are not limited to four pieces as long as they are plural.

The wire-radius-increasing-direction-regulating section 16 is provided with wire passageways 16b and 16b each of which introduces one of the two end sections 12c and 12c of the high-frequency incision wire 12. The previous crimping of the inner periphery wall of the fixture cylinder 15 to project inwardly and the previous crimping of the inner curved surface of the fixture cylinder 15 to impart a greater curvature form the wire passageway 16b. Also, the wire-radius-increasing-direction-regulating section 16 is formed so that the high-frequency incision wire 12 will not move in the direction orthogonal to the axial direction of the fixture cylinder 15. In addition, the wire-radius-increasing-direction-regulating section 16 regulates the direction in which the radius of the high-frequency incision wire 12 increases, while the wire-radius-increasing-direction-regulating section 16 permits rotation of the high-frequency incision wire 12 around the axial line relative to the fixture cylinder 15, and movement of the high-frequency incision wire 12 in the axial direction relative to the fixture cylinder 15.

As illustrated in FIGS. 2 and 3, the direction in which a plurality of wire passageways 16b are disposed coincides with the direction in which the high-frequency incision wire 12 expands.

Figure 7:
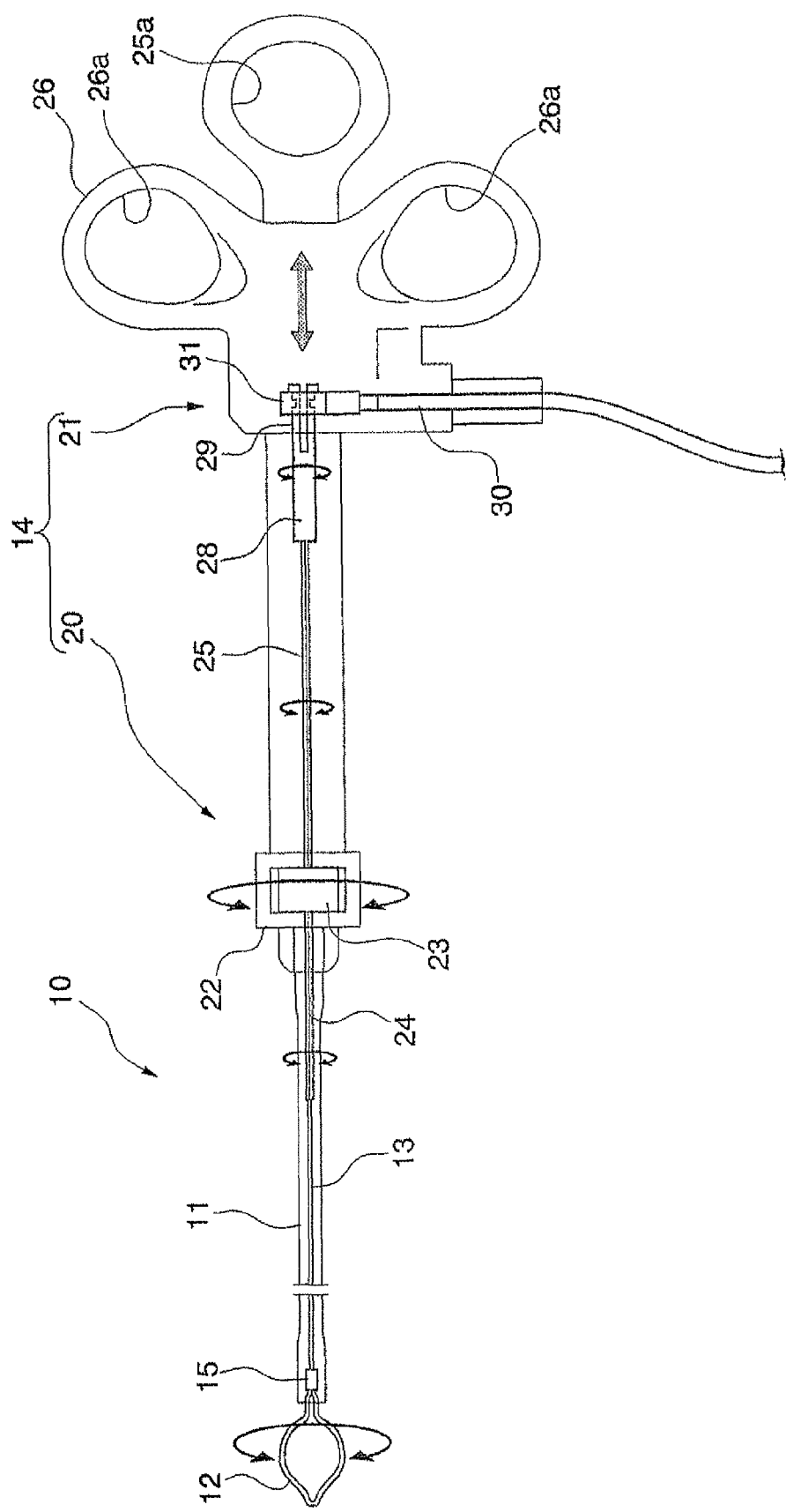
FIG. 7 is a general view of the endoscopic instrument according to the embodiment.

FIG. 7 is a general view of an endoscopic instrument 10 including the maneuvering section 14. As illustrated in the drawing, the maneuvering section 14 is provided with a rotative operation section 20 and a sliding-operation section 21 that are assembled in one unit. The rotative operation section 20 rotates the high-frequency incision wire 12 around the axial line of the sheath 11 via the maneuvering wire 13. The sliding-operation section 21 provided to the proximal end of the rotative operation section 20 slides the high-frequency incision wire 12 in the axial line direction of the sheath 11 via the maneuvering wire 13.

Figure 8:
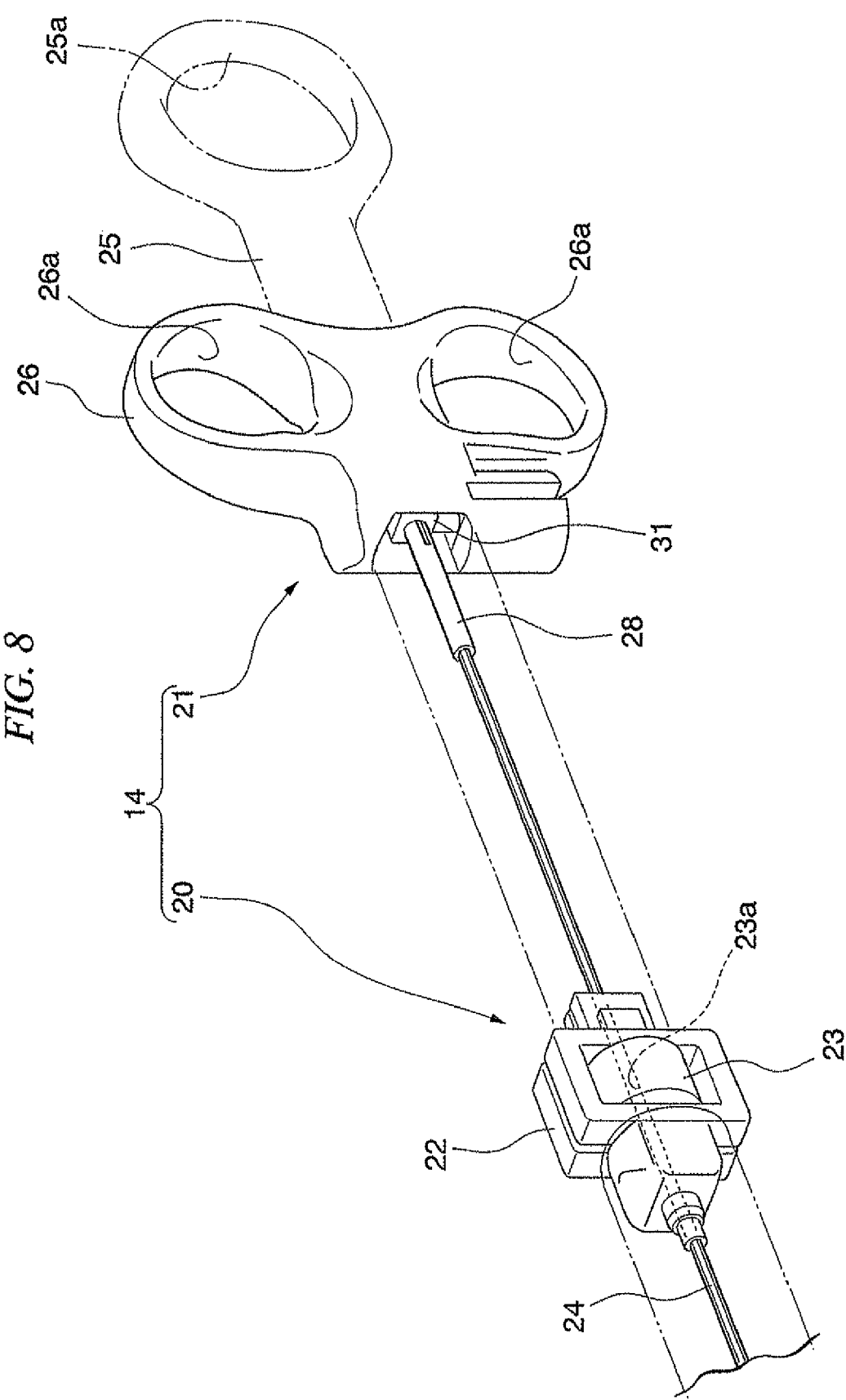
FIG. 8 is a perspective view partly showing the structure of a maneuvering section of the endoscopic instrument according to the embodiment.

FIG. 8 is a perspective view showing the detail of the rotative operation section 20 and the sliding-operation section 21. As illustrated in FIG. 8, the rotative operation section 20 is provided with a rotating-member-supporting casing 22 and a rotating member 23. The rotating-member-supporting casing 22 is fixed to the proximal end of the sheath 11. The rotating member 23, disposed in the rotating-member-supporting casing 22, can rotate around the axial line of the sheath 11 relative to the rotating-member-supporting casing 22 while movement of the rotating member 23 in the axial line direction of the sheath 11 is regulated.

Formed in substantially the center of the rotating member 23 is a polygonal, e.g., hexagonal through hole 23a, through which a rod 24 having the corresponding hexagonal cross-section is inserted. This allows the rotating member 23 to rotate around the axial line of the sheath 11 relative to the rod 24 and to move the rotating member 23 in the axial line direction relative to the rod 24. The rod 24 is coaxially connected to the proximal end section of the maneuvering wire 13.

The sliding-operation section 21 is provided with a maneuvering section main unit 25 and a slider 26, capable of moving the axial line direction of the rod 24, attached to the maneuvering section main unit 25. The maneuvering section main unit 25, fixed to the proximal end of the rotating-member-supporting casing 22 can move the rod 24 capable of rotating around its axial line direction and enclose the rod 24 therein.

Figure 9:
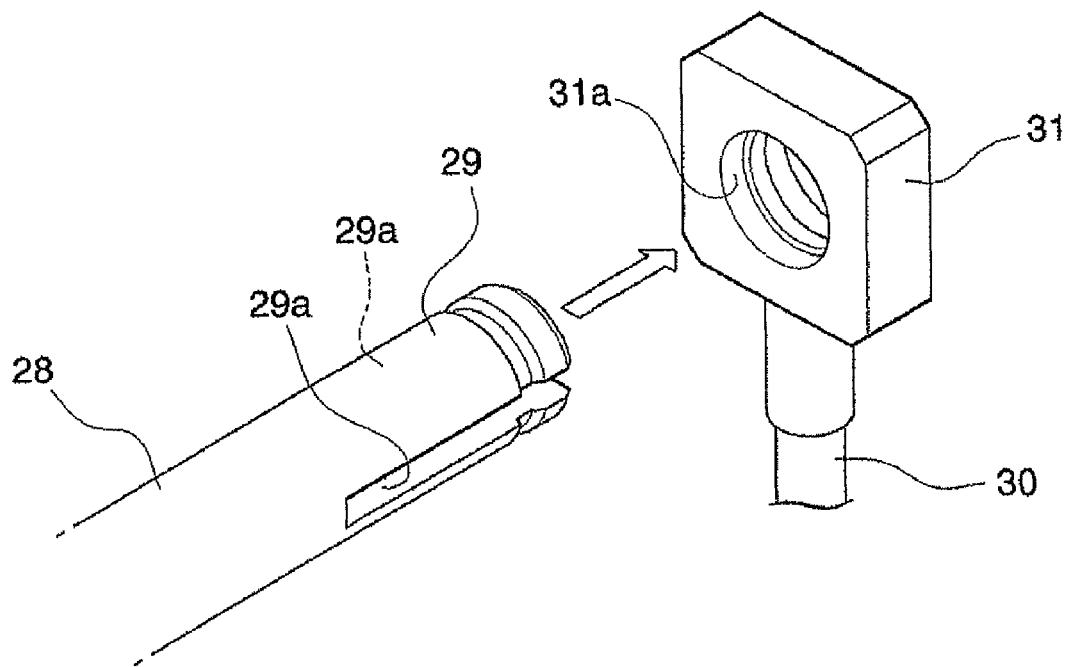
FIG. 9 is a perspective view showing the structure of a maneuvering section of the endoscopic instrument according to the embodiment.

A connecting rod 28 is attached to the proximal end of the rod 24 coaxially. A fitting section 29 has two separated branch sections 29a at the proximal ends of the connecting rod 28 (See FIG. 9). The fitting section 29 is inserted into a fitting hole 31a formed on the inner end base section 31 of the plug 30. The fitting section 29 in this fitting state can rotate around the axial line of the connecting rod 28 relative to the fitting hole 31a of the plug 30 while the movement of the fitting section 29 relative to the connecting rod 28 in the axial line direction is regulated. In addition, the distal end of the plug 30 assembled to the slider 26 is exposed outwardly.

It should be noted that the maneuvering wire 13, the rod 24, the connecting rod 28, and the plug 30 made from conductive material, e.g., metal, can transfer high-frequency electric current introduced from the plug 30 to the high-frequency incision wire 12.

In addition, a finger hook ring 25a is provided to the maneuvering section main unit 25, and a finger hook ring 26a is provided to the slider 26.

Figure 10:
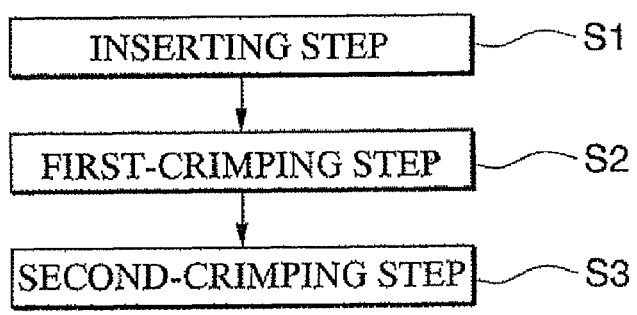
FIG. 10 is a flowchart showing how to fix a high-frequency incision wire to a fixture cylinder in the endoscopic instrument according to the embodiment.

Explained next with reference to FIG. 10 will be a method for fixing the high-frequency incision wire 12 to the fixture cylinder 15 in the endoscopic instrument of the present invention.

To start with, the high-frequency incision wire 12 is cut into a predetermined length; and precurve having a predetermined direction is imparted thereto.

The two end sections 12c, 12c provided to the proximal end of the high-frequency incision wire 12 having precurve are inserted from above and into a hole 15a of the fixture cylinder 15 (insertion step; step S1).

As illustrated in FIG. 5, subsequently projecting punches 18a and 18a in opposed two opposing directions toward the distal end of the fixture cylinder 15 forms the wire-radius-increasing-direction-regulating section 16 (first-crimping step; step S2).

Subsequently projecting four punches 18b each disposed every 90 degrees toward in a middle section in the longitudinal direction of the fixture cylinder 15 in a second-crimping step forms the wire-fixing section 17 (second-crimping step; step S3).

The aforementioned steps allow the high-frequency incision wire 12 to be fixed to the fixture cylinder 15.

Explained next will be a method for incising a lesion site of a patient with an endoscopic instrument 10 having the aforementioned configuration.

To start with, the sheath 11 enclosing the loop section 12a of the high-frequency incision wire 12 and inserted into the channel 2 of the insertion section 1a of the endoscope 1 is inserted into the body cavity of a patient. Partially injecting a normal saline solution if necessary elevates the lesion site found by observation using this state of the endoscope 1.

Subsequently, the slider 26 of the maneuvering section 14 is maneuvered to extend toward the distal end. The maneuvering of the slider 26 transferred to the high-frequency incision wire 12 via the plug 30, the connecting rod 28, the rod 24, and the maneuvering wire 13 cause the high-frequency incision wire 12 to project relative to the distal end of the sheath 11 as illustrated in FIG. 1. The high-frequency incision wire 12 upon projecting restores, i.e., expands, the loop section 12a.

The loop section 12a of this state of the high-frequency incision wire 12 is hooked on the lesion site. Rotating the rotating member 23 of the maneuvering section 14 provides an appropriate angle of rotation to this state of the loop section 12a which is not in parallel with the lesion site, i.e., inclined relative to the lesion site. That is, rotation torque of the rotating member 23 is transferred to the high-frequency incision wire 12 via a hexagonal rod 24 and the maneuvering wire 13, thereby allowing the loop section 12a of the high-frequency incision wire 12 to rotate around the axial line of the sheath 11. Although this state of the connecting rod 28 connected to the rod 24 rotates with the rod 24 rotating around the axial line of the rotating member 23, the plug 30 and the slider 26 will not rotate around the axial line of the rod 24 since the connecting rod 28 capable of rotating relative to the plug 30 is attached to the plug 30.

Therefore, rotating the rotating member 23 can vary the direction of the loop section 12a of the high-frequency incision wire 12 at an arbitrary angle, thereby facilitating the hooking of the loop section 12a onto the lesion site.

Subsequently, the slider 26 is retracted toward the proximal end and the high-frequency incision wire 12 is retracted into the sheath 11 while the distal end of the sheath 11 is pressed to the vicinity of the lesion site. The elevated lesion site is constricted with this state of the high-frequency incision wire 12. Supplying high frequency electric current to this state of the plug 30 can incise the lesion site and normal tissue therearound constricted by the high-frequency incision wire 12.

The fixture cylinder 15 of the endoscopic instrument having the aforementioned configuration, i.e., provided with the wire-radius-increasing-direction-regulating section 16 for regulating the direction in which the radius of the high-frequency incision wire 12 increases; and the wire-fixing section 17, provided in the vicinity of the proximal end relative to the wire-radius-increasing-direction-regulating section 16, for fixing the high-frequency incision wire 12 can direct and fix a plane defined by the loop section 12a at an arbitrary direction without using a specific fixture that positions the loop section of the wire, thereby facilitating the fixing of the high-frequency incision wire 12 using the fixture cylinder 15 by carrying out the aforementioned first-crimping step S2 and a second-crimping step S3.

In addition, the structure of the wire-radius-increasing-direction-regulating section 16 regulating the direction in which the radius of the high-frequency incision wire 12 increases and permitting rotation of the wire around the axial line relative to the fixture cylinder 15 and movement of the wire relative to the fixture cylinder 15 in the axial direction merely regulates the direction in which the radius increases, but the wire-radius-increasing-direction-regulating section 16 does not fix the high-frequency incision wire 12, thereby preventing unnecessary load from being applied to the two end sections 12c, 12c of the high-frequency incision wire between the wire-radius-increasing-direction-regulating section 16 and the wire-fixing section 17.

In addition, the wire passageways 16b, 16b, for guiding each one of the two end sections 12c, 12c of the high-frequency incision wires, provided to the wire-radius-increasing-direction-regulating section 16 can regulate the direction of the high-frequency incision wire, i.e., a plane defined by the expanding loop section 12a.

In addition, the wire passageway 16b formed partially by compressing the inner periphery wall of the fixture cylinder 15 inwardly is susceptible to simpler structure and cost reduction relative to a case in which a separate member is attached to the fixture cylinder 15 to form a wire passageway.

In addition, intervention for polyp, etc. are facilitated; thus, operability improves since the rotative operation section 20 for rotating the high-frequency incision wire 12 and the sliding-operation section 21 for moving the high-frequency incision wire 12 in the axial line direction are assembled to the maneuvering section 14 in one unit. Also reducing the component count and average number of man-hours necessary for assembly can achieve cost reduction.

MODIFIED EXAMPLES

Figure 11:
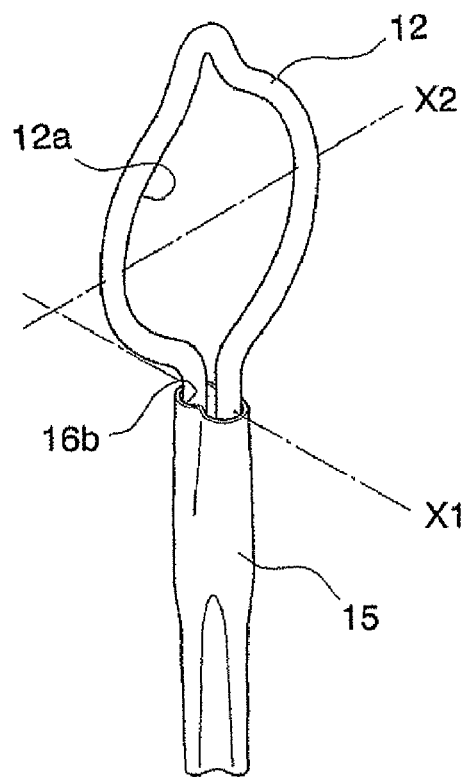
FIG. 11 is a cross-section showing another example of a distal end of the endoscopic instrument according to the embodiment.

FIG. 11 shows a modified example of the high-frequency incision wire 30.

This modified example is different from the aforementioned configuration in that the direction of the plane defined by the loop section 30a of the high-frequency incision wire 30 relative to the fixture cylinder 15 is different.

That is, the direction in which the wire passageways 16b, 16b are disposed coincides with the direction in which the radius of the high-frequency incision wire 12 increases as illustrated in FIG. 2. In contrast, a direction X1 in which wire passageways 30b, 30b are disposed is shifted by 90 degrees relative to a radius-increasing direction X2 of the high-frequency incision wire 12, i.e., the plane defined by the loop section 30a.

Therefore, shifting the direction X1 in which the wire passageways 30b, 30b are disposed relative to the radius-increasing direction X2 of the high-frequency incision wire 12 provides a smooth deformation of the high-frequency incision wire 12 with its restoring force projecting from the sheath 11 wire, thereby resulting in gradual expansion and restoration of the loop section 30a.

Figure 12:
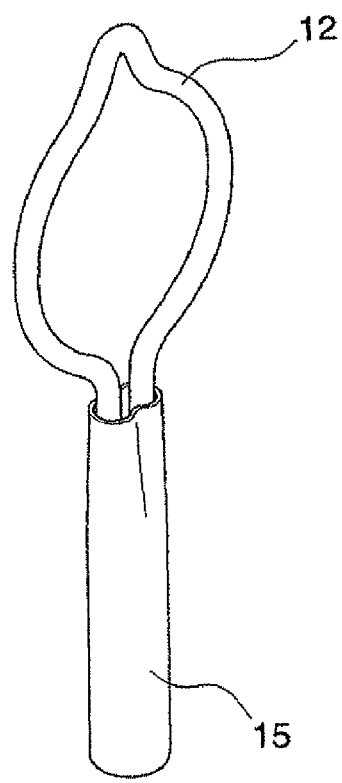
FIG. 12 is a perspective view showing another example of how to manufacture the distal end of the endoscopic instrument according to the embodiment.
Figure 13:
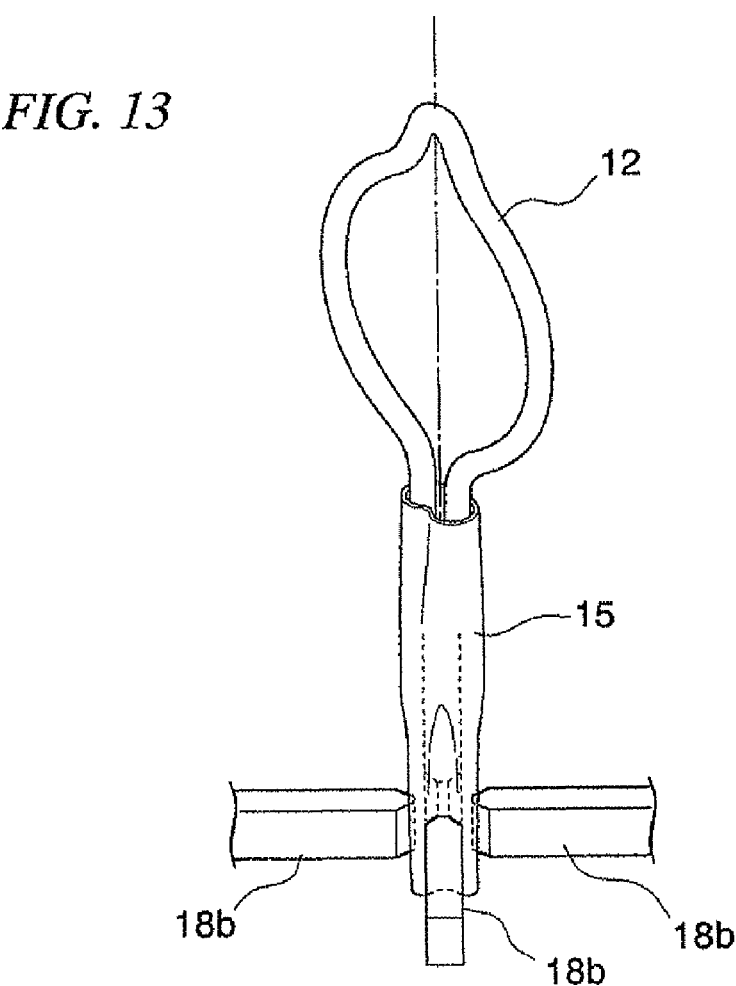
FIG. 13 is a perspective view showing another example of how to manufacture the distal end of the endoscopic instrument according to the embodiment.
Figure 14:
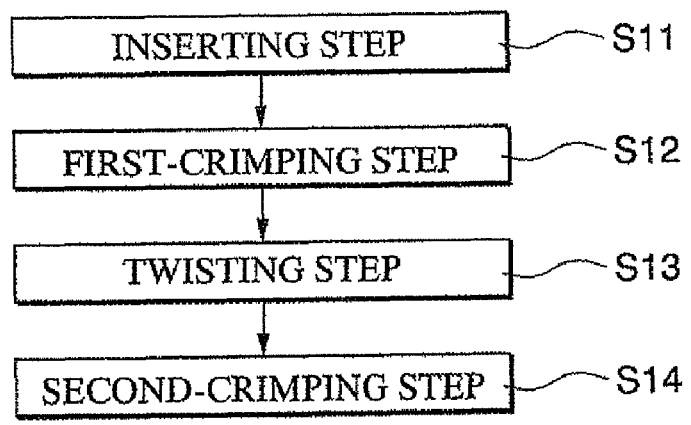
FIG. 14 is a flowchart showing how to manufacture another example of the distal end of the endoscopic instrument according to the embodiment.

FIGS. 12 and 13 are perspective views for explaining how to manufacture the modified example of the endoscopic instrument. FIG. 14 is a flowchart therefor.

The method shown in FIG. 14 for manufacturing the modified example is the same as the manufacturing method that was previously explained with reference to FIG. 10 in that the method of FIG. 14 includes: a step for inserting two ends of the high-frequency incision wire 12 into holes of the fixture cylinder 15 (step S11, see FIG. 12); a first-crimping step for projecting punches in two opposed directions toward the distal end of the fixture cylinder 15 to form the wire-radius-increasing-direction-regulating section 36 (step S12); and a second-crimping step for projecting four punches 18b each shifted by every 90 degrees toward the middle section of the fixture cylinder 15 in longitudinal direction to form the wire-fixing section 17 (step S14, see FIG. 13).

The modified example further includes a twisting step (step S13) for twisting the distal end of the high-frequency incision wire 12 around the axial line of fixture cylinder 15 between the first-crimping step and the second-crimping step.

Therefore, merely adding the twisting step (step S13) between the first-crimping step (step S12) and the second-crimping step (step S14) provides the structure for fixing the high-frequency incision wire 12 to the fixture cylinder 15 as illustrated in FIG. 11 without using a specific fixture.

Here, the technical range of the present invention is not limited to the above embodiment; thus, various modification can be added without deviating from the effects and structures of the present invention.

Figure 15:
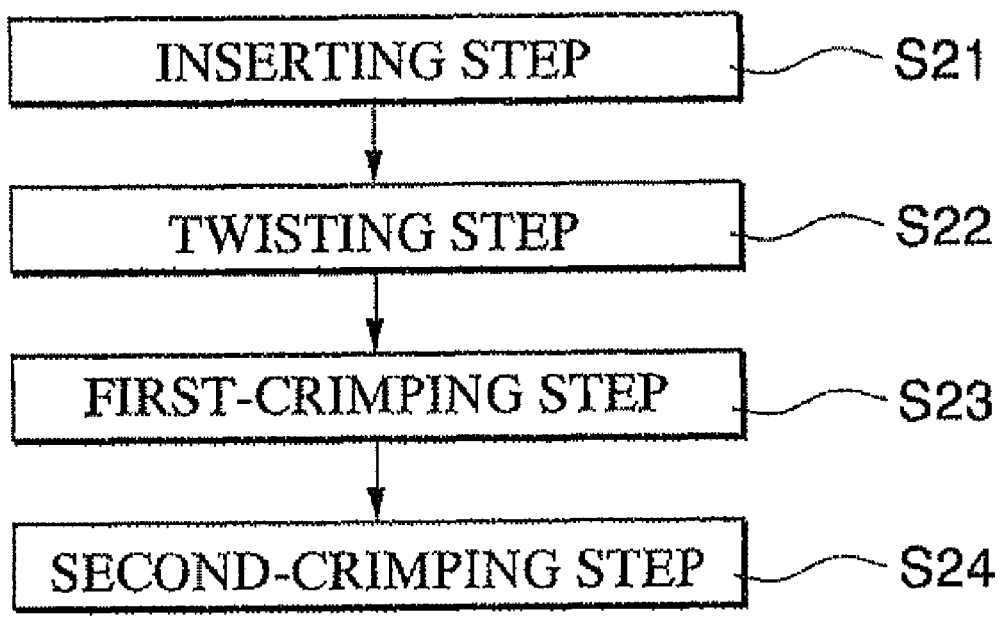
FIG. 15 is a flowchart showing another example of how to manufacture the distal end of the endoscopic instrument according to the embodiment.

The method for manufacturing the modified example as illustrated in FIG. 14 is not limited to a configuration in which the twisting step S13 is included between the first-crimping step S12 and the second-crimping step S14. The endoscopic instrument as illustrated in the modified example may be manufactured by a method including an insertion step S21; a twisting step S22; a first-crimping step S12; and a second-crimping step S24 in order as shown in FIG. 15.

To be more specific, two end sections of a high-frequency incision wire 12 are inserted into two separated guide members which are not shown in the drawing. Subsequently, the two end sections of the high-frequency incision wire 12 are inserted into holes of a fixture cylinder 15 while the end sections of the wires are inserted into the guide members. That is, the insertion step S21 has two steps. Subsequently, the distal end of the wire is twisted around its axial line while the movement of the distal end of the wire in any direction other than the axial line is regulated by the two-separated guide members. This is conducted by the twisting step S22. Subsequent to this step, the method further includes a first-crimping step S23 and a second-crimping step S24. The high-frequency incision wire 12 according to the modified example can be manufactured by this manufacturing method.

The aforementioned embodiment is not limited to a configuration in which the high-frequency incision wire 12 is crimped to be fixed to the fixture cylinder 15. That is, the high-frequency incision wire 12 may be fixed to the fixture cylinder 15 by a brazing method or by the combination of a brazing method and a crimping method.

In addition, the aforementioned embodiment is not limited to a configuration in which the wire-radius-increasing-direction-regulating section 16 is provided to the distal end of the fixture cylinder 15 and the wire-fixing section 17 is provided in the middle of the fixture cylinder 15 in longitudinal length. That is, a wire-radius-increasing-direction-regulating section 16 may be provided in the middle of the fixture cylinder 15 in longitudinal length; and a wire-fixing section may be provided to the proximal end of the wire-fixing section 15.

Also, the present invention is not limited to a configuration in which a part of the wire passageway 16b is formed by projecting the inner periphery wall of the fixture cylinder 15. The wire passageway 16b is formed partially by a separate member other than a component forming the fixture cylinder 15.

What is claimed is:

1. An endoscopic instrument comprising:
    a wire comprising a loop or basket section and two ends disposed proximal to the loop or basket section, wherein the loop or basket section has an expanded state and a contracted state; and
    a fixture cylinder having an internal lumen through which the two ends of the wire are disposed, wherein the fixture cylinder is provided with:
    a wire-radius-increasing-direction-regulating section for regulating the direction in which the radius of the loop or basket section of the wire increases; and
    a wire-fixing section, disposed in the vicinity of a proximal end of the fixture cylinder relative to the wire-radius-increasing-direction-regulating section, for fixing the two ends of the wire; and
    a flexible sheath through which the fixture cylinder and wire are disposed and are capable of freely projecting relative to the flexible sheath, wherein the loop or basket section expands to the expanded state when projected distally from the flexible sheath.

2. The endoscopic instrument according to claim 1, wherein the wire-radius-increasing-direction-regulating section further regulates the direction in which the radius of the wire increases while the wire-radius-increasing-direction-regulating section permits rotation of the wire in an axial direction relative to the fixture cylinder and movement of the wire in an axial direction relative to the fixture cylinder.

3. The endoscopic instrument according to claim 1, wherein the wire-radius-increasing-direction-regulating section is provided with wire passages each guiding one of a plurality of wires.

4. The endoscopic instrument according to claim 3, wherein each wire passage is formed partially by projecting an inner periphery wall of the fixture cylinder inwardly.

5. The endoscopic instrument according to claim 4, wherein the fixture cylinder is made from metal, and the wire-radius-increasing-direction-regulating section is formed by a crimping method.

6. The endoscopic instrument according to claim 5, wherein the wire-fixing section is formed by a crimping method.

7. The endoscopic instrument according to claim 1, wherein the wire-radius-increasing-direction-regulating section is formed to the distal end of the fixture cylinder, and the wire-fixing section is formed in the middle of the fixture cylinder in longitudinal direction.

8. The endoscopic instrument according to claim 1, wherein a maneuvering section for maneuvering the wire is provided with a rotation-maneuvering section for maneuvering rotation of the wire around an axial line; and a sliding-maneuvering section for maneuvering a sliding movement of the wire in the axial line direction, the rotation-maneuvering section and the sliding-maneuvering section are assembled in one unit.

* * * * *